United States Patent [19]

Cheung

[11] Patent Number: 5,215,881
[45] Date of Patent: Jun. 1, 1993

[54] PSEUDORABIES DIAGNOSIS PROBES

[75] Inventor: Andrew K. Cheung, Ames, Iowa

[73] Assignee: The United States of America as represented by the Secretary of Agriculture, Washington, D.C.

[21] Appl. No.: 537,855

[22] Filed: Jun. 13, 1990

[51] Int. Cl.⁵ .................. C12Q 1/70; C12Q 1/68; C12P 19/34; C07H 21/00
[52] U.S. Cl. .................................. 435/5; 435/6; 435/91; 536/24.32
[58] Field of Search .................. 536/27; 435/6, 91, 5

[56] References Cited

U.S. PATENT DOCUMENTS 4,711,850 12/1987 Kit et al. .............................. 435/235

FOREIGN PATENT DOCUMENTS

WO87/01287 3/1987 PCT Int'l Appl. .

OTHER PUBLICATIONS

Jordan Spivak et al. Journal of Virology, vol. 65(12) pp. 6800-6810, Dec. 1991.
Wagner et al. (Dec. 1988) "The Herpes Simplex Virus Latency Associated Transcript is spliced during latent phase infection; Journal of Virology", vol. 62(12) 4577-4585.
H.-J. Rziha et al., "Studies on Reactivation of Latent Pseudorabies Virus from Lymphoid Blood Cells," Abstract, 14th International Herpesvirus Workshop, Denmark (1989).
Andrew K. Cheung, "Cloning of the Latency Gene and the Early Protein O Gene of Pseudorabies Virus," J. Virol. 65(10): 5260-5271 (Oct. 1991).
Gutekunst, D. E. (1979)"Latent Pseudorabies Virus Infection in Swine Detected by RNA-DNA Hybridization" American Journal of Veterinary Research 40(11), pp. 1568-1572.
Falser, N. et al. (1986) Journal of Virology, vol. 57(1), pp. 335-339.
Wagner, E. K. et al. (1988) Journal of Virology, vol. 62(4), pp. 1194-1202.
Rziha, H.-J. et al. (1986) Virology, vol. 155, pp. 600-613.
Andrew K. Cheung, "Fine Mapping of the Immediate--Early Gene of the Indiana-Funkhauser Strain of Pseudorabies Virus," J. Virol. 62(12):4763-4766 (Dec. 1988) (I).
Andrew K. Cheung, "Detection of Pseudorabies Virus Transcripts in Trigeminal Ganglia of Latently Infected Swine," J. Virol. 63(7):2908-2913 (Jul. 1989) (II).
Andrew K. Cheung, "DNA Nucleotide Sequence Analysis of the Immediate-Early Gene of Pseudorabies Virus," Nucl. Acid Res. 17(12): 4637-4646 (1989) (III).
Andrew K. Cheung, "The BamHI J Fragment (0.706 to 0.737 Map Units) of Pseudorabies Virus is Transcriptionally Active During Viral Replication," J. Virol. 64(3): 977-983 (Mar. 1990) (IV).

Primary Examiner—Margaret Moskowitz
Assistant Examiner—Lisa Bennett
Attorney, Agent, or Firm—M. Howard Silverstein; John D. Fado; Curtis P. Ribando

[57] ABSTRACT

Regions in the pseudorabies virus genome in the unique long region and the internal repeat sequence contain nucleotide sequences which are unique to latent infection of the virus. These regions are the basis for constructing nucleic acid probes and antigens useful in distinguishing latent pseudorabies infection from productive infection.

11 Claims, 3 Drawing Sheets

PSEUDORABIES DIAGNOSIS PROBES

BACKGROUND OF THE INVENTION

1. Field of the Invention

Pseudorabies (Aujeszky's disease) is caused by a herpesvirus belonging to the genus alphaherpesvirinae. It is a contagious and sometimes fatal disease of swine. Infection during gestation can result in fetal death and abortion. It is estimated that annual losses due to pseudorabies is as high as 60 million dollars in the United States. This economic impact has resulted in a decision by the swine industry and regulatory officials to eradicate the pseudorabies virus (PRV).

During the initial phase of the acute disease, PRV replicates in the upper respiratory tract. Virus can then disseminate by vascular, lymphoid and nervous tissues [D. P. Gustafson, In Diseases of Swine, ed. by A. D. Leman, et al., 6th edition, pp. 274-289, Iowa State University Press, Ames, Iowa]. Infections virus and/or viral genome can be detected from lung, tonsil, brain stem, trigeminal ganglia and peripheral blood lymphocytes [F. Wang et al., J. Leukocyte Biol. 43: 256-264 (1988); G. Wittmann et al., Arch. Virol. 66: 227-240 (1980); H. J. Rhiza In Latent Herpes Virus Infections in Veterinary Medicine, ed. by G. Wittman et al., Martinus Nijhoff publishers, The Hague pp. 429-444 (1984); H. J. Rhiza et al., In Proc. 14th International Herpes Workshop, Nyborg, Denmark, pp. 55 (1989)]. Upon cessation of clinical signs and recovery from infection, the virus is not eliminated from the animal and persists with the animal indefinitely. Sometimes, the infection is subclinical and goes unnoticed. The animal also becomes a carrier of pseudorabies. In either case, the virus exists in various cell types of the animal in a noninfectious form and is commonly known as a latent infection. The complete viral genome is present but fails to replicate fully to produce infectious virus. The latent virus can reactivate spontaneously or be induced to reactivate by exogenous stimuli, the carrier animal disseminates infectious virus to susceptible animals which may result in death of the animal or establishment of new PRV carriers. Thus, the latent virus is the source and reservoir of the disease and is regarded as an obstacle to the successful control and eradication of PRV.

This invention relates to the identification and generation of nucleic acid probes that are capable of distinguishing between productive and latent infections.

2. Description of the Prior Art

The mechanisms of establishment, maintenance and reactivation of the latent pseudorabies is not known at the present time; but it is quite clear that the latency-reactivation cycle contributes to the perpetuation of PRV in the swine population. Although several methods for detecting latent PRV infection in swine has been described, there is no available diagnostic method which is both sensitive and convenient. Direct experimental evidence for the existence of latent PRV has been obtained by in vitro reactivation of latent virus following tissue explantation [A. Sabo et al., Acta Virol. 29: 208-214 (1976); D. E. Gutekunst et al., Am. J. Vet. Res. 41: 1315-1316 (1980); G. W. Beran et al., J. Am. Vet. Med. Assoc. 176: 998-1000 (1980)]. A major drawback of this method is the need for sterile, viable tissues in the assay. This is also complicated by the use of vaccine viruses that are defective in the thymidine kinase gene, for these viruses can establish a latent infection but do not reactivate as readily. In vivo reactivation following daily administration, over a course of several days, of very high doses of corticosteroids has been used successfully to reactivate latent PRV [W. L. Mengeling, Am. J. Vet. Res. 50: 1658-1666 (1989); J. R. Van Oirschot et al., Am. J. Vet. Res. 45: 567-571 (1984); R. E. Mock et al., J. Comp. Med., 45: 56-59 (1981)]. The method does not appear to work in all cases, and the effects of the associated severe immunosuppression can be a complicating factor. Nucleic acid hybridization such as solution and blot hybridization techniques have been used [D. E. Gutekunst, Am. J. Vet. Res. 40: 1568-1572 (1972); H. J. Rhiza et al., Virology 155: 600-613 (1986); R. G. McFarlane et al., Am. J. Vet. Res. 46: 1133-1136 (1985); Belak et al., J. Vet. Med. 34: 519-529 (1987)], but they are not capable of detecting extremely low quantities of latent DNA. In situ hybridization is inherently sensitive since it can detect latency at the single cell level [H. J. Rhiza et al., supra, 1984; D. L. Rock, Arch Virol. 98: 99-106 (1988)]; unfortunately, the method is extremely labor intensive. The most promising technique to date is the polymerase chain reaction (PCR) technique capable of amplifying the target DNA sequence by a millionfold [Belak et al., Arch. Virol. 108: 279-286 (1989)]. Since the amount of PRV genome present in latently infected swine is exceedingly low, the target DNA sequence remains a limiting step for determining pseudorabies latency even with the PCR amplification method.

The PRV genome is a linear, duplex DNA molecule with a molecular weight of approximately $90 \times 10^6$ [T. Ben-Porat et al., "Molecular Biology of Pseudorabies Virus," In B. Roizman (ed.), The Herpesviruses, Vol. 3, Plenum Publishing Corporation, New York, pp. 105-173 (1985)]. It is estimated that the genetic material is capable of coding for 50 to 100 viral genes. The transcription pattern of PRV in infected cells is extremely complex; however, the genes are expressed in a coordinated, and temporally regulated manner [L. T. Feldman et al., Virology 116: 250-263 (1982); Virology 97: 316-327 (1979); S. Ihara et al., Virology 131: 437-454 (1983); and T. Rakusanova et al., Virology 46: 877-889 (1971)]. In general, herpesvirus genes are categorized into three classes: immediate-early (IE), early, and late genes. The IE genes are transcribed immediately upon infection and do not require de novo protein synthesis. Transcription of early genes depends on IE protein expression and occurs before viral DNA replication. The late genes are transcribed after the onset of viral protein and DNA synthesis.

During herpesvirus latency, a restricted region of the viral genome is transcriptionally active. RNAs denoted as latency-associated transcripts (LATs) are detectable in animals latently infected with the virus [Stevens et al., Science 235: 1056-1059 (1987)]. For pseudorabies virus, the LATs are located downstream of the immediate-early (IE180) gene and in the antiparallel orientation. Since the pseudorabies LATs are the only genetic elements present during latency, it is expected that they play a role in the establishment, maintenance and/or reactivation of the latent virus. As such, the LATs are specific for latency and they are present in higher quantity than the latent genome; and therefore, a better target for detection.

Patent No. PCT/US86/01804 entitled "Pseudorabies Virus Deletion Mutants and Vaccines Containing Same" assigned to Syntrovet Incorporation has indicated the importance of the junction region between the unique long and internal repeat region for the attenuation of PRV. However, there is no description of its involvement in PRV latency. This is not surprising, since the latency-associated transcripts for herpes simplex virus were first described in 1987, and those for PRV were not described until 1989 [first by Cheung, J. Virol. 63: 2908-2913 (July 1989); then by Lokengard et al., Arch. Virol. 110: 129-136 (1990)].

In summary, there are no convenient diagnostic probes for PRV latency.

SUMMARY OF THE INVENTION

I have now discovered and taken advantage of nucleotide sequences of the genes uniquely expressed during PRV latency. By comparing map locations, DNA fragments or the unique nucleotide sequences themselves to those of the genes expressed during a productive infection, nucleic acid probes that are capable of distinguishing between a productive and latent infection can be generated. Moreover, expression vectors incorporating the probes can also be used to transform appropriate hosts and to thereby produce the corresponding antigens encoded by the sequences. These antigens would be useful in diagnostic assays to detect the presence of latent PRV in clinical samples.

In accordance with this discovery, it is an object of the invention to provide a sensitive and convenient alternative to existing techniques for diagnosis of latent PRV.

It is also an object of the invention to identify logical candidate regions in the PRV genome for developing nucleic acid probes useful for discriminating latent PRV infection from productive infection.

It is further object of the invention to provide nucleic acid probes and antigens useful in the clinical diagnosis of latent PRV infection.

In conjunction with detecting latent PRV infection in individual animals, it is an object of the invention to enable monitoring the spread of PRV in herds of swine and other susceptible livestock animals.

Still another object of the invention is to provide a diagnostic basis for designing an effective control program for PRV in agricultural environments.

Other objects and advantages of this invention will become readily apparent from the ensuing description.

GLOSSARY

For purposes of this invention, the following standard abbreviations and terms used herein have been defined below. Also included are a listing of biological materials and reagents mentioned in the specification.

ABBREVIATIONS bp=base pairs
cDNA=complementary deoxyribonucleic acid
DNA=deoxyribonucleic acid
IE=immediate-early gene of PRV
MDBK=Mardin-Darby bovine kidney cells
EDTA=ethylenediaminetetraacetic acid
PCR=polymerase chain reaction
PRV=pseudorabies virus
RNA=ribonucleic acid
mRNA=messenger ribonucleic acid
SSC=saline sodium citrate
[α-$^{32}$P]UTP=$^{32}$P-labelled uridine triphosphate

TERMS

DNA or RNA sequence: A linear series of nucleotides connected one to the other by phosphodiester bonds between the 3' and 5' carbons of adjacent pentoses.

hybridization: the pairing together or annealing of complementary single-stranded regions of nucleic acids to form double-stranded molecules.

nucleic acid probe: a DNA fragment or a single-stranded piece of DNA or RNA that can be used to detect, by hybridization or complementary base-pairing, a target nucleic acid sequence which is homologous or complementary.

nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

oligonucleotide: a linear series of 2–100 deoxyribonucleotides or ribonucleotides connected one to the other by phosphodiester bonds between the 3' and 5' carbons of adjacent pentoses.

oliogonucleotide probe: see nucleic acid probe restriction site: a nucleotide sequence, usually 4 to 6 base pairs long, which is recognized and susceptible to cleavage in a specific fashion by a restriction enzyme.

sequence: two or more DNA or RNA nucleotides in a given order.

BIOLOGICAL MATERIALS AND REAGENTS cDNA libraries

λgt10=cDNA library of total RNA from latent PRV infection

ZAPII=cDNA library of mRNA from productive PRV infection

Restriction Enzyme

BamHI

Cleavage Site

5'..G GATCC..3'

Strains of Pseudorabies Virus

Becker
Indiana-Funkhauser (In-Fh).

DETAILED DESCRIPTION OF THE INVENTION

In preparation for developing nucleic acid probes for detecting latent PRV, the first step was to determine that there are indeed latency-associated transcripts (LATs) in tissue of infected animals which are specific to the latent state of PRV. Thereafter, the RNA transcripts were isolated and employed in the construction of cDNA libraries to be used in the selection of PRV latency related clones. It is from these clones that regions of nucleotide sequences have been identified for constructing suitable probes. Moreover, the cloned sequences may be inserted into expression vectors for production of antigens useful in diagnostic assays.

Figure 1:
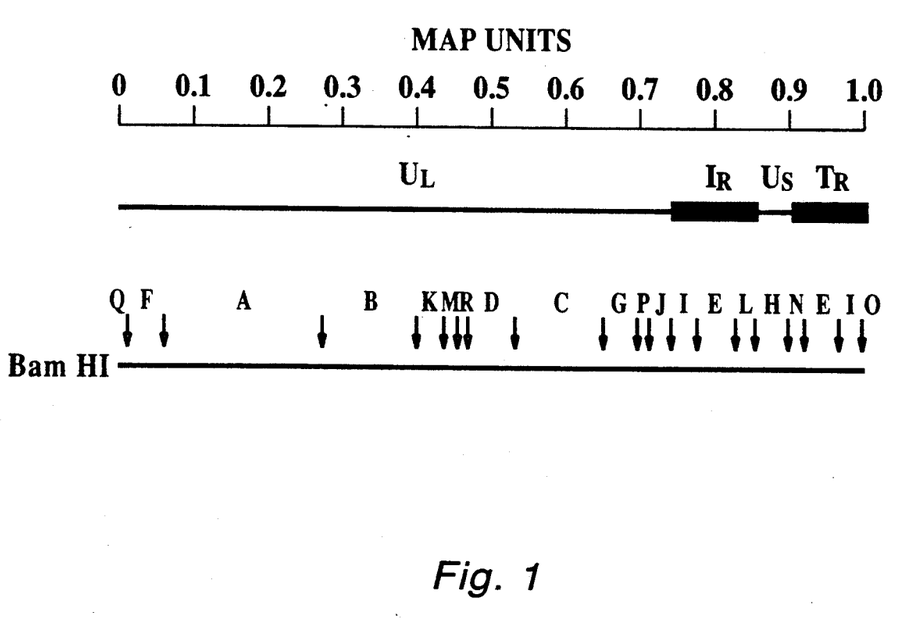
FIG. 1 illustrates the genomic organization and restriction map for BamHI for a typical PRV.

Referring to FIG. 1, the PRV genome organization from left to right is as follows: a unique long region ($U_L$), an internal repeat sequence ($I_R$), a unique short region ($U_S$) and a terminal inverted repeat sequence ($T_R$). FIG. 1 also shows the BamHI restriction map.

As reported in Cheung [J. Virol. 63, supra], two poly-(A)+RNAs (2.0 and 0.95 kb) have been found to be present in the trigeminal ganglia of a sacrificed pig during latency. These two transcripts are partially colinear and of opposite polarity to the IE gene, in an area (0.706 to 0.737 map units) in which no PRV transcripts have been reported before; in addition, they overlap the PRV IE180 mRNA. The fact that there is some evidence that the LATs are present selectively in latently infected tissues suggests that they may play a role in the establishment and/or maintenance of viral latency. In Cheung [J. Virol. 64: 977–983 (March 1990), evidence is presented that the BamHI-J fragment is transcriptionally active during viral replication as well as during latency. However, it is not clear from the data in Cheung (J. Virol. 64, supra) whether any identical transcripts are synthesized under these two apparently mutually exclusive conditions. On one hand, the similarities between these two sets of RNAs suggest that the PRV LATs are actually late PRV transcripts synthesized during viral replication and that latency is induced when the normal infection cycle is interrupted by specific factors after the synthesis of LATs. On the other hand, these RNAs may be different at the molecular level.

In accordance with this invention, it has now been established that there are, indeed, LATs which are specific to the latent state of PRV. As described in more detail in Example 1 below, total RNAs isolated from trigeminal ganglia of a pig latently infected with PRV was used to construct a first cDNA library (λgtlo). A second cDNA library (ZAPII) was constructed from mRNA isolates derived at various stages throughout the replicative cycle of PRV in tissue culture. Both libraries were screened with a BamHI-J probe to identify positive clones. From the λgtlo library, pseudorabies specific sequences present in the positive clones were isolated and subcloned in Bluescript SK+ plasmids. From the ZAPII library, the pseudorabies sequences were rescued as Bluescript SK- plasmids. The PRV nucleotide sequences of the positive clones were determined and aligned with the nucleotide sequences of PRV genome. More than 50 cDNA clones have been characterized as having originated from the latent infection library or the productive infection library. These clones have also been grouped according to the BamHI fragment from which the nucleotide sequences originate. The groupings are shown in FIG. 3.

A strategy for constructing a single-stranded oligonucleotide probe within the scope of the invention is initiated by predetermining the probe's length. It is envisioned that oligonucleotide probes useful herein would range in size from about 15 to 50 bases, with the preferred size being about 17 to 35 bases. A sequence of the predetermined length, occurring within one of the cDNA clones isolated from latent PRV infection is then selected.

Given below in the Sequence Listing as SEQ ID NO. 1 is a region encompassing the 3′ end of the BamHI-G fragment, the 5′ end of the J fragment and all of the intervening P fragment, hereafter referred to as "BamHI G-P-J". Within this region, there are sequences at either end which are not common to characteristic clones of both types of infection.

Given below in the Sequence Listing as SEQ ID NO. 2 is a region encompassing the 3′ end of the BamHI-J fragment and all of the I fragment, hereafter referred to as "BamHI J-I". There are also sequences at either end of this region which are not common to characteristic clones of both types of infection.

Given below in the Sequence Listing as SEQ ID NO. 3 is the sequence derived from fragment BamHI-P and -J as the result of a splicing event unique to latency. Of course the intervening sequence would be present in the PRV genome or clones derived from productive infection.

Under appropriate conditions of stringency, probes of the invention will bind to the LATs but not to transcripts characteristic of productive infection. This specificity makes these probes useful for the detection of PRV latency.

Alternatively, larger single-stranded RNA probes, up to several kilobases in length, can be prepared by cloning appropriate genomic fragments into plasmids. Hybridization is then carried out with RNA samples followed by treatment with nuclease to digest nonannealed sequences. Probes of this type are useful in identifying substantially homologous mRNA transcripts of proper orientation as described in more detail in Example 2.

To enable detection, the probes described above may be bound to a radioactive, enzymatic, or organic label by any conventional procedure in the art. The labelled probes hybridized to the target transcripts can thereby be detected in a southern, northern, solution, or in situ hybridization assay. Probes hybridized to target sequences can also be amplified by PCR and visualized by a gel electrophoresis analysis.

The DNA sequences of this invention may be used in many expression vectors to produce the antigens encoded by the DNA or may be engineered to produce antigens that are fused to amino acids unrelated to pseudorabies. The amino acid sequence derived from these DNA sequences may also be used to prepare synthetic peptides that are useful as diagnostic antigens.

The antigens, their antibodies and the DNA sequences of this invention may be used in methods and means designed to detect the presence of latent pseudorabies virus in various blood samples. For example, the antigens produced or the antibodies raised against them may be employed in radioimmunoassay or enzyme-linked immunosorbent assay (ELISA).

The following examples are intended only to further illustrate the invention and are not intended to limit the scope of the invention which is defined by the claims.

EXAMPLE 1

Virus and Cell Culture

The Indiana-Funkhauser (In-Fh) strain of PRV was grown on Mardin-Darby bovine kidney (MDBK) cells cultivated in Eagle minimum essential medium supplemented with 10% fetal bovine serum.

Trigeminal Ganglion Tissue of Swine Pigs were exposed to PRV (Becker strain) intranasally. Six weeks postinfection, when virus could not be recovered from the infected animals, the trigeminal ganglia were removed for analysis.

Preparation of RNAs and Construction of cDNA Libraries

The trigeminal ganglia of a pig latently infected with the PRV Becker strain were homogenized with a polytron (Brinkmann Instruments, Inc.) in a solution of 5M guanidine isothiocyanate, 0.1M 2-mercaptoethanol, 25 mM sodium citrate (pH 7.0), and 0.5% N-lauroyl-sarcosine. Total RNAs were isolated from the lysate by centrifugation through a 5.7M cesium-chloride cushion. A λgt10 cDNA library of $9 \times 10^5$ independent clones was constructed by standard procedure using total RNAs primed with oligo-d(T). Total RNAs were also isolated from the tissue culture (MDBK) cells infected with PRV In-Fh. Poly(A)+RNAs were isolated by affinity chromatograph on oligo-dT cellulose. Equivalent amounts of poly(A)+RNAs throughout the replicative cycle (0, 2, 4, 6, 8, 10, and 12 hr postinfection) were mixed and used for the construction of a ZAPII cDNA library by standard method. This library has $1.3 \times 10^6$ independent clones.

Screening the cDNA Libraries to Select for Pseudorabies Latency Related Clones

The λgt10 and ZAPII cDNA libraries were first screened with $^{32}$P-labelled nick-translated BamHI-J probe by standard method. The positive clones were then purified. From the λgt10 library, pseudorabies specific sequences present in the positive clones were isolated and subcloned into Bluescript SK+plasmids. From the ZAPII library, the pseudorabies sequences were rescued (by standard method) as Bluescript SK−plasmids. The PRV nucleotide sequences of the positive clones were determined, and the nucleotide sequences derived from the latent PRV and from the productive infection In-Fh clones were aligned with the sequences of the PRV genome. These clones fall into three groups and are denoted as group -A, -B and -D in FIG. 3. A clone from group-A was then used as probe to screen the ZAPII library, and clones belonging to group-C were isolated. More than 50 cDNA clones have been characterized.

Figure 3:
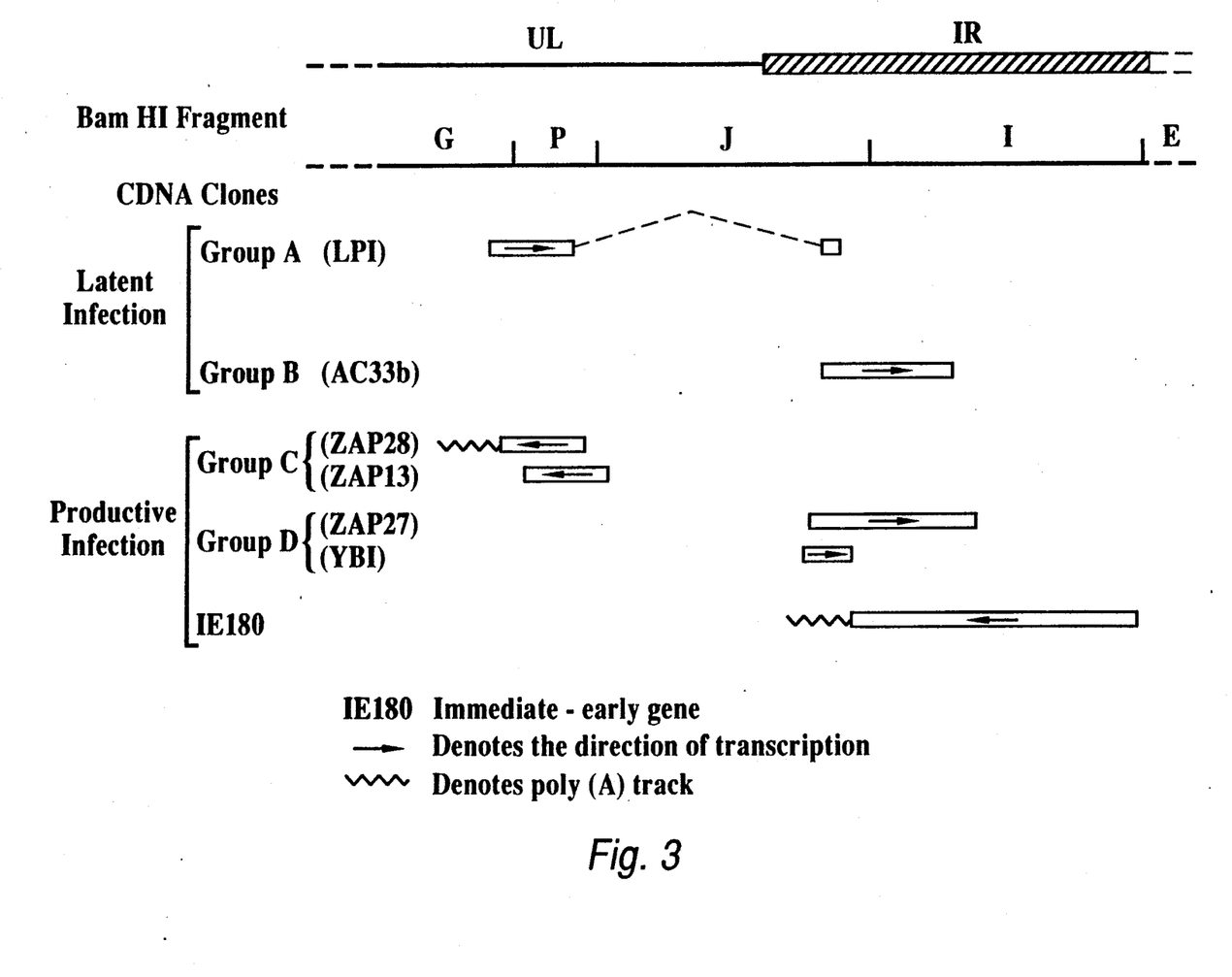
FIG. 3 illustrates the transcription pattern of PRV during latency and replication in the BamHI-G, -P, -J, -I, and -E region.

Clones of groups A and B are isolated from the λgt10 library (latent tissue RNA). Group-A clones contain sequences that originate in BamHI-G fragment, continue rightward into BamHI-P fragment and then spliced to the right-hand portion of BamHI-J fragment. Group-B clones contain sequences 3' (or rightward) of the splice junction in BamHI-J and continue into BamHI-I fragment. Some of these clones have a poly(A) track.

Clones of groups-C and -D are isolated from the ZAPII library (productive infection RNA). Group-C clones contain sequences that originate in BamHI-J, continue leftward into BamHI-P and terminate in BamHI-G with a poly(A) track. Group-D clones contain DNAs similar to group-B clones except that the sequences originate 5' (or leftward) of the splice junction in BamHI-J fragment.

EXAMPLE 2

Virus and Cell Culture

The PRV In-Fh was grown on MDBK cells cultivated in Eagle minimum essential medium supplemented with 10% fetal bovine serum.

Trigeminal Ganglion Tissue of Swine

Pigs were exposed to PRV (Becker strain) intranasally. Six weeks postinfection, when virus could not be recovered from the infected animals, the trigeminal ganglia were removed for anlaysis. The negative control (normal) pig was obtained from a certified PRV-negative herd.

Preparation of RNAs

PRV-infected and uninfected tissue culture cells or trigeminal ganglion tissues of swine were homogenized with a polytron (Brinkmann Instruments, Inc.) in the presence of guanidinium thiocyanate. Total RNAs were isolated from the lysate by centrifugation through a CsCl cushion. Poly(A)+RNAs were selected by oligo(dT)-cellulose chromatography. For enrichment of PRV mRNA, MDBK cells were treated with 100 μg of cycloheximide per ml before and during PRV infection as described further, below. Cycloheximide is an inhibitor of protein synthesis.

Radioactive Probes

Single-stranded runoff RNA probes of known specificity were generated from linearized plasmids containing PRV DNA in the presence of [α-$^{32}$P]UTP (New England Nuclear Corp.) by using T3 or T7 polymerase in accordance with supplier protocol (Stratagene). The entire BamHI-J (approximately 4.8 kb) genomic fragment was cloned into the BamHI site of the Bluescript SK+plasmid in both orientations for the generation of probes IIIa and IIIb, of opposite polarity. The single-stranded probes generated were slightly longer than the PRV DNA insert because the transcripts contained some plasmid sequences at the 5' and 3' ends.

S1 Nuclease Analysis

Hybridization of [$^{32}$P]UTP-labelled single-stranded RNA probes ($10^5$ cpm) was carried out with the various RNA samples (5 to 10 μg). The hybridization buffer contained 40 mM piperazine-N,N'-bis(2-ethanesulfonic acid) (PIPES) (pH 6.4), 1 mM EDTA (pH 8.0), 0.4M NaCl, and 80% formamide. The samples were heated at 85° C. for 10 min and cooled to 50° C. overnight. The annealed samples were digested with 500 U of S1 nuclease (Pharmacia, Inc.) per ml at 37° C. for 30 min. The treated samples were analyzed with either a 6% polyacrylamide sequencing gel [A. M. Maxam et al., Methods Enzymol. 68: 499–560 (1980)] or a 1% agarose gel after chemical and heat denaturation [G. K. McMaster et al., Proc. Natl. Acad. Sci., USA, 74: 4835–4838 (1977)]. The polyacrylamide sequencing gels were wet while the agarose gels were dry when exposed to X-ray film.

Figure 2:
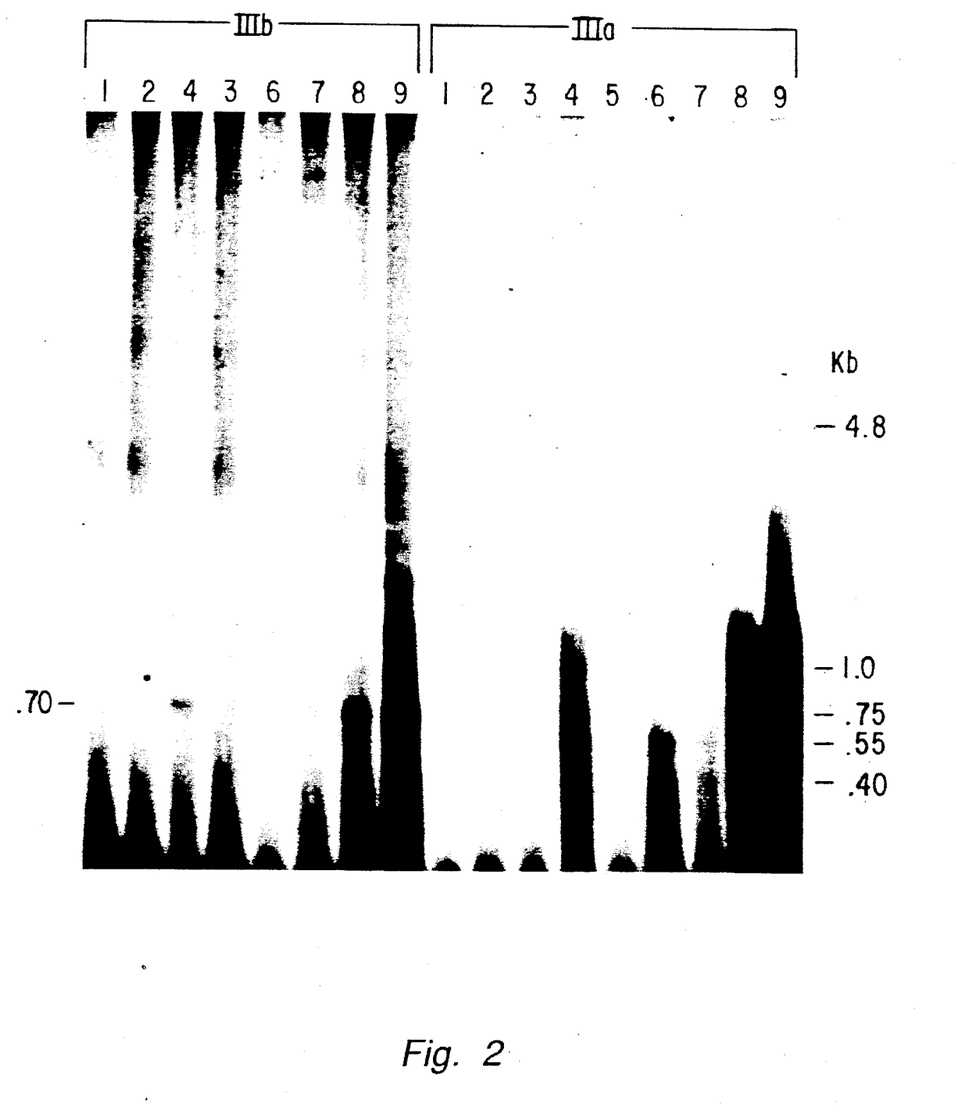
FIG. 2 is an autoradiogram with single-stranded probes generated from BamHI-J fragment (IIIa and IIIb) capable of discriminating latent and replicating PRV.

The results of the above experiment are illustrated in the autoradiogram of FIG. 2. The treatments of the samples represented by the various lanes of the autoradiogram are as follows:

1—mock infection of tissue culture (MDBK) cells.
2—2 hour postinfection in the presence of cycloheximide.

4—cells were infected in the presence of cycloheximide. The drug was then removed for 4 hours (infection process resumes after removal of the drug).

3—cells were infected in the presence of cycloheximide. The drug was then removed for 1 hour.

6—RNA from a pig latently infected with pseudorabies virus.

5—control RNA from normal pig.

7, 8, and 9—3 hours, 6 hours, and 9 hours post infection in the absence of cycloheximide.

Interpretation of the autoradiogram is as follows:

(1) lanes 4, 7, 8, 9—RNAs from replicating pseudorabies are positive for both probes IIIa and IIIb; and (2) lane 6—RNAs from latently infected pig are positive for probe IIIa, but negative for IIIb.

From these results, it can be concluded that probes IIIa and IIIb can be used to distinguish latent PRV infection from productive PRV infection based on the presence of a unique LAT corresponding to the BamHI-J genomic fragment.

It is understood that the foregoing detailed description is given merely by way of illustration and that modification and variations may be made therein without departing from the spirit and scope of the invention.

SEQUENCE LISTING (1) GENERAL INFORMATION
  (i) APPLICANT: CHEUNG, ANDREW K.
  (ii) TITLE OF INVENTION: PSEUDORABIES DIAGNOSIS PROBES
  (iii) NUMBER OF SEQUENCES: 3
  (iv) CORRESPONDENCE ADDRESS:
  (A) ADDRESSEE: ANDREW K. CHEUNG
      USDA-ARS-MWA
      NATIONAL ANIMAL DISEASE CENTER
  (B) STREET: P.O. BOX 70
  (C) CITY: AMES
  (D) STATE: IA
  (E) COUNTRY: U.S.A.
  (F) ZIP: 50010
  (v) COMPUTER READABLE FORM:
  (A) MEDIUM TYPE: 5¼" DOUBLE-SIDED, DOUBLE-DENSITY MAXELL DISKETTE
  (B) COMPUTER: IBM COMPATIBLE
  (C) OPERATING SYSTEM: DOS
  (D) SOFTWARE: DNASIS
  (vi) CURRENT APPLICATION DATA:
  (A) APPLICATION NUMBER: P.C. 2030.90
  (B) FILING DATE:
  (C) CLASSIFICATION:
  (vii) PRIOR APPLICATION DATA: N/A
  (A) APPLICATION NUMBER: N/A
  (B) FILING DATA: N/A
  (viii) ATTORNEY/AGENT INFORMATION:
  (A) NAME: RIBANDO, CURTIS P.
  (B) REGISTRATION NO.: 27,976
  (C) REFERENCE/DOCKET NO.: P.C. 2030.90
  (ix) TELECOMMUNICATION INFORMATION:
  (A) TELEPHONE: FTS 360-4513
      COM 309/685-4011, X513
  (B) TELEFAX: COM 309/685-4128
  (C) TELEX: N/A (2) INFORMATION FOR SEQ. ID NO. 1
  (i) SEQUENCE CHARACTERISTICS:
    (A) LENGTH: 1831
    (B) TYPE: nucleic acid
    (C) STRANDEDNESS: single
    (D) TOPOLOGY: linear

| | | | | | |
|---|---|---|---|---|---|
| 5' TATATAATCC | CCGGTCCGCG | CTCCGCCCAC | CCATCACAGC | AGCCGCGGAC | 50 |
| TGCGCGCCGG | AGCGGTCCAT | CTCGCCAGCC | AGCCAACCAC | CAGCCGCCCA | 100 |
| GCCGACCCGA | GAGCCCCGAG | AGCCAGACTC | CCTCAGCCAT | AGAAGACACC | 150 |
| GGGCGGGAGA | GACGGACTGA | AAAAATATAT | CTTTTTTTAT | TTTGTCTGGG | 200 |
| CCTGGAGACC | CGCAGCAGGA | GCGGAGGTGG | GTGCGGGGCC | GGGAGCCGGA | 250 |
| GCAGGACCGG | GAACAGGAAC | AGGAACAGGA | ACAGGAACAG | GAACAGGAGT | 300 |
| GGGGCCGGGA | GCAGGAGCAG | GAGCGGGAGC | CGAAGTGGGG | GCAGGAGCGG | 350 |
| CGGCGGCCGC | AGCAGCAACA | GGGTCGCCCC | AGTCCGCGGC | GAGGAAGAGG | 400 |
| GAGCTCAGTC | GTCGTCCTGG | GTGAGGTCGA | TGAAGATGGT | AGCGGAGCGG | 450 |
| GGGGATCCCG | ACGAGCTAGA | CGCCGGAGGC | CCGCCCCGGG | GGGCGGCGGT | 500 |
| CTCGGGGGCA | GAGGCAGAGG | GCGACGGGCG | CCGCATCGAG | GAGGAGGGTG | 550 |
| AAGACGAGGG | GGAGGAGCGA | GCCGAAGCGG | CGGTGTTCGC | CGACCCCGGG | 600 |
| CCGGCCCCGG | CCCCCGAGGC | ACCATGCTGC | GCAGAGGACC | CCTCGCCGGA | 650 |
| CGATGGCGCC | TCCGGAGTCT | CGCCCTGGGC | CTGTCCGCCC | GTCCGGCCGC | 700 |
| GTCGCAGGCA | CCGGGTCCGT | CTCTGCTCGC | GCCTCAGCAC | GGCCGCCCGT | 750 |
| CGGGCCCTGC | GCGGGAGCG | CCTGGGCGCC | GGCCTCTGGT | CGTCCGCGGA | 800 |
| CTCGGAGGCC | TCCGTCAGAT | CCTCCGTGTG | CACCCCGCTG | CTCGAGGCGC | 850 |
| CCGAGTCTTC | CTCGTCGGGG | GAAGACACCT | CAGAGTCAGA | GTGTGCCTCG | 900 |
| GACTCGGACG | TGTCGATATA | GTTCACACCC | TGGTGGCTCA | TCGGGGCTCG | 950 |
| CCTCTGCATC | CGCCGCATCC | ACTGCGCCGA | TATGTCAAAC | AGCGTATCGA | 1000 |
| CGAGGGCGTG | GGTGTTTGCC | CCAAACATGG | GGAGCATGGC | CTCGGTCACG | 1050 |
| CGCTGGCGGT | TCATCCCGTG | CTCCTGGATA | ATCTCGACGA | TGTTGTCCAC | 1100 |
| GACGGCCTCG | CGGATGGGGT | CGCTCTCGAT | GACCGTCGAG | ACCTGCCCAT | 1150 |

SEQUENCE LISTING

| | | | | | |
|---|---|---|---|---|---|
| AAAGCCAGTT | GAAGACGGGG | ACTCTGGGGC | GGGCGCGAGA | CCCAGAGGGC | 1200 |
| CAGCCCTGCC | CTTCGGCCTC | CTCGTGGCGC | ACCTCCTCGG | TATAGTCTTC | 1250 |
| ACCCCAGATG | ACCGCGAATC | CCCCCCCTAC | CGGCTCATCC | TCTTCCCCGT | 1300 |
| CGACATCCGT | CGCCCCCTCC | ACGGGCGTCT | CCACAAACGA | AGCGTCGCTG | 1350 |
| TCCACGTGGT | GGAGGATGGA | GGTGACGCGG | GCCTTGCACA | GCGGGCAGGC | 1400 |
| GGTGCTCGTC | AGGGTCCAGC | GCTGGATGCA | GTCCAGACAG | AACTTGTGCA | 1450 |
| TGCACGGCAG | CGTCTGCGCC | TCGGTGGCCG | CGACGTCCAG | GCAGATGGGG | 1500 |
| CAGTCCATGA | CGGATCCCCC | GCTCTCACCC | CTGGGTCCGT | CGCCGCCCCG | 1550 |
| CGGTGCGTGC | GACGCCCGCG | AACCCCCGCG | CCACAACACA | CCGGCACCAC | 1600 |
| CACCGCCATC | ATCGTCCCCC | CTCTCCACAT | ACACGCTCGC | ACTCGGGCCA | 1650 |
| CACGCTCCCG | TCCTCCGCCG | CCACCCTCCC | AGCCTCCCAG | CCTCGCGGGT | 1700 |
| CCTCGGGACG | ACCGCCGCTC | ACCCCGACGG | GGGGACTGGG | ACAGGGAGCA | 1750 |
| GGGGGGGAGG | AGGACGGGGG | GGAAGAGGGG | AACGCGAGCG | CGGCGCACCC | 1800 |
| CGTCGCCGTC | CGTGGTGGCG | GGCACGCACC | C 3' | | 1831 |

(2) INFORMATION FOR SEQ. ID NO. 2
(i) SEQUENCE CHARACTERISTICS:
  (A) LENGTH: 2721
  (B) TYPE: nucleic acid
  (C) STRANDEDNESS: single
  (D) TOPOLOGY: linear

| | | | | | |
|---|---|---|---|---|---|
| 5' CGACCACCCG | GGACCACCAC | CACCAACACC | GCCACCACCC | CCCCCCTTCA | 50 |
| CGCACACACT | TTACTACTAT | CACCACCAGG | GGGCGATGGT | TGCAACGGCA | 100 |
| GTTCCCTGTA | CTGACCACCA | CCGTGTTTTT | TTTTCTTTTT | CTCTCTTTCC | 150 |
| CCCCCCCTCG | ACCACCGCAG | GACCACCATC | GTCTAACTCC | CACCCGGGAC | 200 |
| CACCGGGACC | CTCGGACCA | TCTACCTCCC | ACCAGGACCC | GCCGGGACCA | 250 |
| CCAACACCGT | CCACCTCCCA | CCACCACCAT | CATCATCAAG | GACCCCCAAC | 300 |
| ATCCCCAAGA | CCCTCTACTT | CTTCCCACCA | AGACCCTCCA | GGAGGAGGAC | 350 |
| CCCCATCTGC | TGAGACCCAC | CACCACCACC | AAGACCCACC | AGGAGGAGGA | 400 |
| CCCCCATCCA | CTTCTTCCCA | TCACCACCAC | CAAGACCCTC | CAGGAGGAGG | 450 |
| ACCCCCGTCA | CCCCCACCAA | GACCCTCCAC | CTCTTCTTCT | TCCTCCCACC | 500 |
| AGGGACCCCC | ATCCACAAGA | CCACCTCCAC | CCCAGAGACC | ACCGCCAAGA | 550 |
| TGGCCGCCTC | CATCTCCCCA | AAAAATCTCA | GAGACTCGGG | CTGGTTCAGA | 600 |
| AAATACAGCA | CAAACTTTAT | TTTCTCACTC | TGAAAATAAA | CTCTTTTCTC | 650 |
| ACCCGATGGG | AGAAGGAGGA | GAAGGGGACC | GGGGGACCGC | GGGAGGAGAA | 700 |
| GGGGACCGGG | ACGATCCTCG | GCCGCCGAGC | CCTCCGCCGC | GGCCGCCGCC | 750 |
| GCCGCTTCCA | CCACCGCCGC | CACCTCCGCC | GCCGCCGCAG | CCACCTCCGG | 800 |
| CCGGGGGATC | CGCGCGGAGG | AGAAGGAGAG | GAGGAGGAGG | AGGGCCACCG | 850 |
| GGCCGGGGAG | GCAGGCGCCG | GGGAGGCAAG | CGCCGCCGGG | CCGAGGGGAC | 900 |
| CGAGGCCGCC | GCCGCGGACG | CAGAGGAGGA | GGAGGACGGG | GACGAGGACG | 950 |
| AGGACGAGGA | CCGGGCCGAG | GACGAGGGGA | GAGAAGACGG | AGGAGAAGGG | 1000 |
| CCTCGAGGAG | CCGGTGGAGG | GGCCGGAGAG | TCAGAGTCAG | AGTCAGAGTC | 1050 |
| CAGCCGGGCC | GAGGGGGCGC | CCCGCTCAGC | GGAGCAGCAG | GTAGGGGTTG | 1100 |
| CCGGCGTCCT | CGGCCTCCTC | GTCGTCCGAG | ATGGCCTCCA | CCTTGATGGG | 1150 |
| CCCGAGCGGG | CCGCGGGGCC | GGCCGTCGCC | GCCGCGGAAG | CCGACGATCT | 1200 |
| CCACCGCGGC | AGAGTCCTCC | CCGTCCTCGC | CGGGCCCCCG | GGCGCCCGAG | 1250 |
| GGCCGGTGGG | TCTCCACGGC | GCCGCGGCGG | GCGGCGGGGA | CGCTGGTCTC | 1300 |
| GAAGGGCGCA | AAGTCCCAGC | GCACGGCCGG | CGGGGCGCCC | GCGGCCGCGA | 1350 |
| GGGCGCCCGG | GGCCAGCACC | AGCGGGGCGG | CCTCGGCGTC | GGGCTCCAGC | 1400 |
| AGCGCCGCGG | CGCAGAAGGC | GCGCAGCTCG | GCCGGCAGGC | CCTCGGGGCC | 1450 |
| GCGGAGCTCG | GCGAGGCCCC | GGCGGCCGCA | GGAGACGAAG | ACGGGCCGCA | 1500 |
| GCGGGGCGCC | GAGCCCCCAG | CGGTTGGCCG | CGCGGTGCCC | GAAGGCGGCG | 1550 |
| CCCGCGTCAA | AGTCCGGGTC | CCCGAGCCCG | AGCGCGGAGC | GCTGGCGGGC | 1600 |
| CATGTCCTTG | CAGCCGTCCA | CGGTGGGGAG | CACGCGCTCG | CGGTAGGCGC | 1650 |
| GCGGCGGCAG | CGGGACCGGG | GTCCGGGCGT | CGGCGCGGGT | GCTCACCGTG | 1700 |
| TAGCGCACGT | TGTCCTGGCG | GCAGAGGCGC | AGCGGCTCGG | CCCCGGGGTG | 1750 |
| CAGGCGGGCG | AAGGAGGCCT | CCACGCGGGC | GAAGCAGGCC | GGGCCCACGA | 1800 |
| TGGAGCTCGA | GTCCAGGACG | GCCGCGCGGA | GCTCGCGGCA | CTCGGGCCAG | 1850 |
| CGCACGGCGC | ACTGGGCGGC | CGGGTCCAGG | CGGGCGCGGA | CGTAGACGTG | 1900 |
| GTAGTCCCCC | ACGGCCGGGC | CGTCCGCGGG | CCAGTCCTCG | ATGGTGTCCA | 1950 |
| GCACGATGAG | CCGGCGCCGC | GCCGCGCCGA | GCCGCGAGCA | GAGGTACTCG | 2000 |
| ACGGCGCCGG | CGAAGCCGAG | GTCCCGCGCC | GAGAGCAGCA | GCACCCCCTG | 2050 |
| GGCGTTGAGG | CGGCCGATGT | CGGGGCGCCC | GGTCCAGTTC | CCGGCCCAGG | 2100 |
| CGTGCGAGTC | CGGCGTGCAG | AGGCGGTGGG | CGAAGGCGGC | GAGCAGCGCC | 2150 |
| GAGAGGCCGC | CGCGGCGCGG | GTCCCAGGCC | GGGCGCGGGG | CGCCCTCGGC | 2200 |
| GGGCTCGGCG | CAGAGCTCCT | CGTGGGGCAG | CGGGTCGTAG | AGCACCACCA | 2250 |
| CGCGCACGTC | CTCGGGGTCG | GCTATCTGCC | GCATCCAGGC | GGCGCGGCGG | 2300 |
| CGGAGCGGGG | CGCCCGCGGC | CCCGCGGCGC | GCGGCGATGT | GCGCCAGGGC | 2350 |
| GGCCGGGTCG | AAGGTGAGCG | CCGGGCGCCA | GAGTTCGGGG | AAGACCTCCT | 2400 |
| GGTCCACGAG | GGCGCGGGCC | ACCTCGGGCG | GGCAGTAGGC | GGCGAGGGCC | 2450 |
| GCGGCGGAGG | GCCGCGGCGT | GTGGGTCTCG | CCGGCCGGGA | CGCGGCGGAA | 2500 |
| GCCGCCGTCG | GGCGCGGGGT | GCTCGGGCAT | GGGCCCGAGC | GGGCGCCGGA | 2550 |
| GCCGGTCGTC | CTCGGAGGAG | GAGGAGGAGG | AGGAGGAGGA | CACGAGCGCG | 2600 |
| GGAGCGGGGT | CCGGAGCGGG | CCCGAGTCCG | AGGGAGCGGC | GCTTGCGCCG | 2650 |
| GGGCCCCCGG | TCCTCTTCGT | CGTCGCGGTG | GCCGTGGCCG | TCCCCGCGGA | 2700 |
| GGGCCGAGCC | GGAGAGCCCC | T 3' | | | 2721 |

(2) INFORMATION FOR SEQ. ID NO. 3
(i) SEQUENCE CHARACTERISTICS:
  (A) LENGTH: 100
  (B) TYPE: nucleic acid
  (C) STRANDEDNESS: single
  (D) TOPOLOGY: linear

SEQUENCE LISTING

Sequence identification number 3: Splice junction of the latency-associated transript.
Nucleotide 1451 to 1511 - from sequence ID-1.
Nucleotide 169 to 207 - from sequence ID-2.

```
1451  TGCACGGCAG CGTCTGCGCC TCGGTGGCCG CGACGTCCAG GCAGATGGGG
               1511 169
                  *  *
      CAGTCCATGA C GGACCACCAT CGTCTAACTC CCACCCGGGA CCACCGGGA 207
```

I claim:

1. A purified single-stranded DNA or RNA oligonucleotide probe consisting of: (1) a sequence constituting the BamHI-P-J splice junction identified in SEQ ID NO. 3, (2) a sequence constituting bases from SEQ ID NO. 1 contiguous to, and 5' from said splice junction, and (3) a sequence constituting bases from SEQ ID NO. 2 contiguous to and 3' from said splice junction, wherein said probe is useful for distinguishing between the pseudorabies virus transcription pattern during latency and the pseudorabies virus transcription pattern during replication.

2. A probe as described in claim 1 which encompasses all of the bases in SEQ ID NO. 3 which are 5' from the splice junction.

3. A probe as described in claim 1 which encompasses all of the bases in SEQ ID NO. 3 which are 3' from the splice junction.

4. A probe as described in claim 1 which encompasses all of the bases in SEQ ID NO. 3 which are both 3' and 5' from the splice junction.

5. A method for detecting latent pseudorabies virus in a biological material sample comprising:
   (a) contacting isolated nucleic acid derived from said sample under hybridization conditions with a purified single-stranded DNA or RNA oligonucleotide probe consisting of: (1) a sequence constituting the BamHI-P-J splice junction identified in SEQ ID NO. 3; (2) a sequence constituting bases from SEQ ID NO. 1 contiguous to, and 5' from said splice junction; and (3) a sequence constituting bases from SEQ ID NO. 2 contiguous to and 3' from said splice junction, whereby said probe will hybridize to a target RNA transcript unique to latent infection in said sample; and
   (b) detecting said hybridized probe in a hybridization assay.

6. A method as described in claim 5 wherein said probe encompasses all of the bases in SEQ ID NO. 3 which are 5' from the splice junction.

7. A method as described in claim 5 wherein said probe encompasses all of the bases in SEQ ID NO. 3 which are 3' from the splice junction.

8. A method as described in claim 5 wherein said probe encompasses all of the bases in SEQ ID NO. 3 which are both 3' and 5' from the splice junction.

9. A method as described in claim 5 wherein said biological material sample is trigeminal ganglia.

10. A method as described in claim 5 herein said biological material sample is blood or a blood fraction.

11. A method for producing by polymerase chain reaction a nucleic acid having the sequence of SEQ ID NO. 3.

* * * * *